US006977075B2

(12) United States Patent
Hasan et al.

(10) Patent No.: US 6,977,075 B2
(45) Date of Patent: Dec. 20, 2005

(54) PHOTOSENSITIZER CONJUGATES FOR TARGETING INTRACELLULAR PATHOGENS

(75) Inventors: Tayyaba Hasan, Arlington, MA (US); Jerome Gross, Waban, MA (US); Gerard J. Nau, Medford, MA (US)

(73) Assignee: The General Hospital Corporation, Charlestown, MA (US)

( * ) Notice: Subject to any disclaimer, the term of this patent is extended or adjusted under 35 U.S.C. 154(b) by 0 days.

(21) Appl. No.: 10/413,179

(22) Filed: Apr. 14, 2003

(65) Prior Publication Data

US 2003/0224002 A1 Dec. 4, 2003

Related U.S. Application Data

(62) Division of application No. 09/418,910, filed on Oct. 15, 1999, now Pat. No. 6,610,298.
(60) Provisional application No. 60/104,584, filed on Oct. 16, 1998, provisional application No. 60/115,976, filed on Jan. 15, 1999.

(51) Int. Cl.$^7$ ............... A61K 39/395; A61K 39/04; C12N 1/12; C07B 47/00
(52) U.S. Cl. ............... 424/178.1; 424/9.362; 424/9.61; 424/168.1; 424/180.1; 424/182.1; 424/248.1; 435/863; 435/253.1; 540/145
(58) Field of Search ............... 424/9.362, 9.61, 424/168.1, 180.1, 178.1, 182.1, 248.1; 435/863, 435/253.1; 540/145

(56) References Cited

U.S. PATENT DOCUMENTS

| | | | |
|---|---|---|---|
| 5,091,385 A | | 2/1992 | Gulliya et al. |
| 5,332,567 A | | 7/1994 | Goldenberg |
| 5,389,378 A | | 2/1995 | Madden |
| 5,489,590 A | * | 2/1996 | Gulliya et al. ........... 514/224.8 |
| 5,512,675 A | | 4/1996 | Tang et al. |

OTHER PUBLICATIONS

Soukos et al. (1998) Antimicrob. Agents Chemother. 42(10): p. 2595-2601.
Hryhorenko et al. (1998) Immunopharacology 40:231-240.
Korbelik et al. (1991) Cancer Res 51:2251-2255.
Korbelik et al. (1991) Br J Cancer 64(3):508-512.
Elmer et al. (1987) J Surg Oncol 34:113-119.
Brassuer et al. (1999) Photochem Photobiol 69(3):345-352.
de Vries et al. (1999) J Pharmacol Exp Ther 289(1)528-534.
Hamblin et al. (2000) Photochem Photobiol 72(4):533-540.
Hamblin & Newman (1994) J Photochem Photobiol B 23:3-8.

Korbelik et al. (1993) Photochem Photobiol 58(5):670-675.
Warren and Body, Ch. 3, *Tuberculosis*, Eds. MD Rossman and RR MacGregor, 1995, McGraw-Hill, New York.
http://www.sanger.ac.uk/Info/Press/020301.shtml.
Besra and Chatterjee, Ch. 20, *Tuberculosis: Pathogenesis, Protection, and Control*, Ed. BR Bloom, 1994, American society for Microbiology, Washington, D.C.
Andersen and Brennan, Ch. 21, *Tuberculosis: Pathogenesis, Protection, and Control*, Ed. BR Bloom, 1994, American society for Microbiology, Washington, D.C.
Bloom and Fine, Ch. 31, *Tuberculosis: Pathogenesis, Protection, and Control*, Ed. BR Bloom, 1994, American society for Microbiology, Washington, D.C.
Schein and Huebner, Ch. 5, *Tuberculosis*, Eds. MD Rossman and RR MacGregor, 1995, McGraw-Hill, New York.
Ratledge, Ch. 5, *The Biology of Mycobacteria*, vol. 1 Ed. C Ratledge and J Stanford, 1982, Academic Press, London.
Winder, Ch. 8, *The Biology of Mycobacteria*, vol. 1 Ed. C Ratledge and J Stanford, 1982, Academic Press, London.
http://www/hc-sc.gc.ca/pphb-dgspsp/msds-ftss/msds103e.html.
Malik et al. "New Trends in Photobiology (Invited Review) Bactericidal Effects of Photoactivated Porphyrins-An Alternative Approach to Antimicrobial Drugs" Journal of Photochemistry and Photobiology, B: Biology, 5 (1990) 281-293.
Soukos, N. et al. "Targeted Antimicrobial Photochemotherapy" Antimicrobial Agents and Chemotherapy, vol. 42, Oct. 1998 2595-2601.
Gross et al., (1958) "The heat precipitation of collagen from neutral salt solutions: Some rate-regulating factors" J. of Biol. Chem. vol. 233, Nos. 1-3, pp. 355-360.
Ridley et al. (1983) "Experimental epithelioid cell granulomas tubercle formation and immunological competence: an ultrastructural analysis" J of Pathol. vol. 141, No. 1, pp. 97-112.

* cited by examiner

*Primary Examiner*—Rodney P Swartz
(74) *Attorney, Agent, or Firm*—Edwards & Angell, LLP; Amy M. Leahy

(57) ABSTRACT

The methods of the invention can be used to treat mycobacterial infections, or any disease or disorder that is caused by (or aggravated by) an intracellular pathogen. Accordingly, the invention features methods for treating a subject who has a disorder that is associated with an intracellular pathogen by administering, to a subject, a molecular conjugate that includes a photosensitizer (a term used herein to refer to a light activatable compound) and a targeting moiety, the targeting moiety being capable of targeting the conjugate to the intracellular pathogen.

14 Claims, 2 Drawing Sheets

FIG. 2A
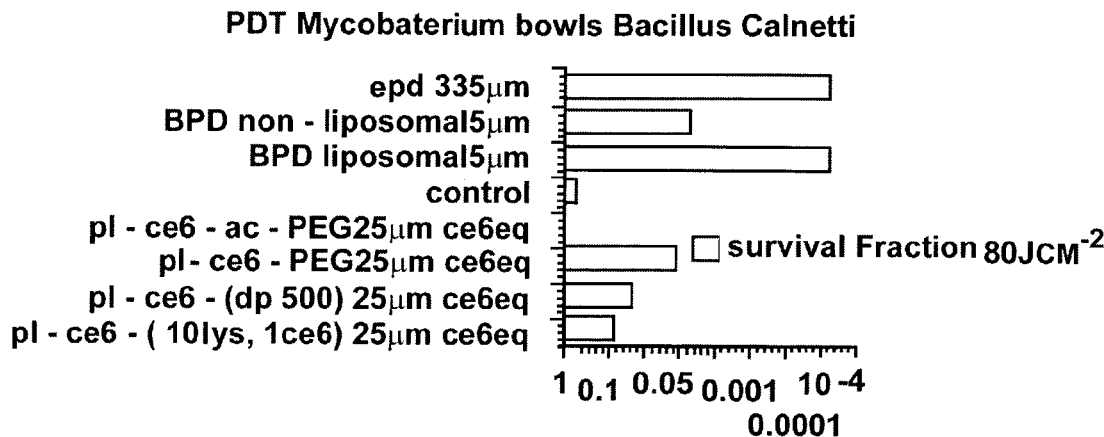
FIG. 2B
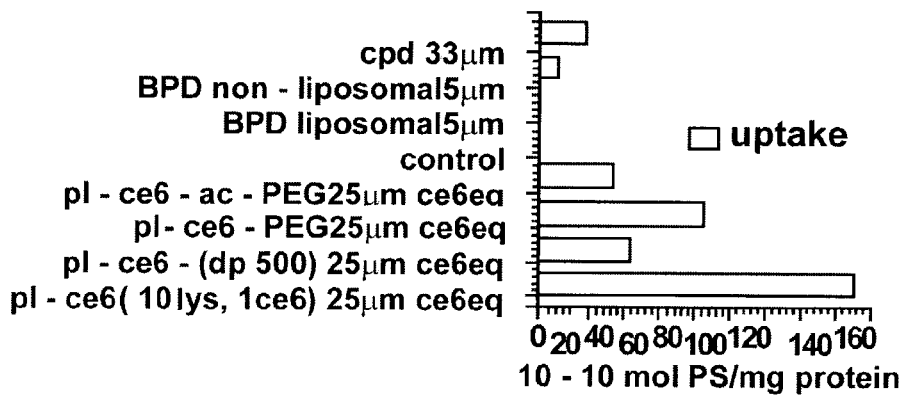
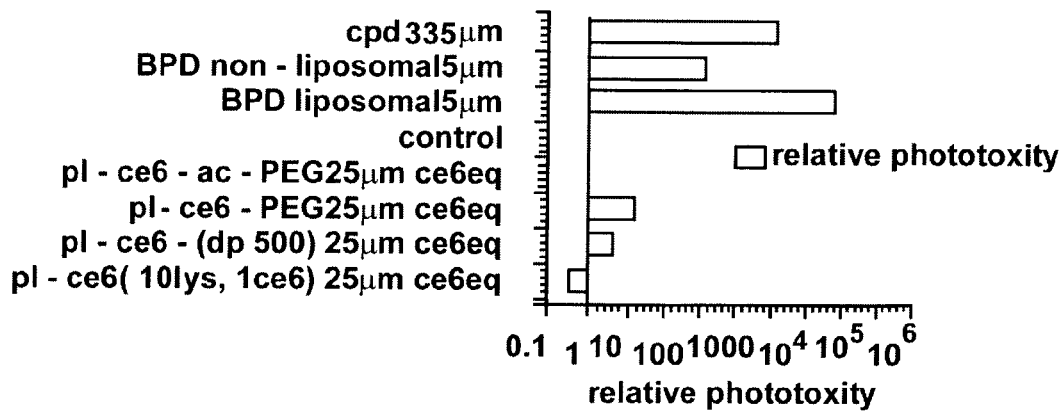
FIG. 2C

PHOTOSENSITIZER CONJUGATES FOR TARGETING INTRACELLULAR PATHOGENS

This is a Division of U.S. application Ser. No. 09/418,910, filed on Oct. 15, 1999, now U.S. Pat. No. 6,610,298, which claims the benefit of U.S. provisional application No. 60/104,584, filed on Oct. 16, 1998, and U.S. provisional application Ser. No. 60/115,976, filed Jan. 15, 1999, which are hereby incorporated by reference in their entirety.

STATEMENT OF RIGHTS TO INVENTIONS MADE UNDER FEDERALLY SPONSORED RESEARCH

This invention was made with Government support under Contract No. N0014-94-I-0927 awarded by the Department of Defense. The Government may have certain rights in this invention

BACKGROUND OF THE INVENTION

The invention relates to a molecular conjugate that includes a photosensitizer and a targeting moiety, and to methods of using the conjugate.

Infectious diseases continue to generate substantial medical problems. This is due, in part, to the emergence of strains of bacteria that are resistant to multiple antibiotics, newly discovered viral diseases, and the spread of diseases caused by fungi and protozoa. For example, the recent emergence of multi-drug resistant strains of *Mycobacterium tuberculosis*, the underlying cause of tuberculosis, is generating a public health problem of epic proportion. Computer modeling studies and field surveys of geographically isolated human communities indicate that tuberculosis may become endemic in host populations having as few as 200 contiguous individuals (a dramatic contrast with diseases such as measles and smallpox, which are maintained only within communities having more than 200,000 contiguous individuals). Moreover, the immune response to *M. tuberculosis* is not eradicative; infected individuals may develop lifelong chronic diseases or latent infections that serve as long-standing reservoirs of contagion.

SUMMARY OF THE INVENTION

Following infection, mycobacteria are phagocytosed by macrophages where they are "sheltered" from many antibiotic drugs and from the subject's immune system. This is especially true in pulmonary tuberculosis, where infected macrophages gather in intrapulmonary granulomas.

The methods of the invention can be used to treat mycobacterial infections, or any disease or disorder that is caused by (or aggravated by) an intracellular pathogen. Accordingly, the invention features methods for treating a subject who has a disorder that is associated with an intracellular pathogen by administering, to the subject, a molecular conjugate that includes a photosensitizer (a term used herein to refer to a light activatable compound) and a targeting moiety, the targeting moiety being capable of targeting the conjugate to the intracellular pathogen. In one embodiment, the subject is treated with a conventional therapy (such as an antibiotic-based therapy) and a molecular conjugate that includes a photosensitizer and a targeting moiety. The targeting moiety is so named because it can target the conjugate to the intracellular pathogen or to the infected host cell (e.g., a macrophage).

Accordingly, the invention features a method for treating a subject having a disorder associated with an intracellular pathogen that includes administering to the subject an antibiotic and a molecular conjugate (which can include a photosensitizer or a photosensitizer and a targeting moiety that targets the conjugate to the intracellular pathogen). The molecular conjugate can be administered before, during, or after the antibiotic is administered. As in other embodiments, the intracellular pathogen can be a bacterial cell (such as a mycobacterium, e.g., *Mycobacterium tuberculosis*). The pathogen can be within a phagocyte (e.g., a macrophage). The method can also include irradiating the subject, preferably using a wavelength that causes the photosensitizer to produce a cytotoxic effect. Preferably, the cytotoxic effect is substantial enough to kill at least 50%, more preferably at least 70%, and most preferably at least 90% of the pathogenic cells. The source of the irradiation can be any of the sources described herein, for example, a laser.

In another embodiment, the invention features a method for killing a Mycobacterial cell by contacting the cell with a molecular conjugate that includes a photosensitizer and irradiating the cell with light having a wavelength that causes the photosensitizer to produce a cytotoxic effect. The method can further include administering a molecular conjugate that includes both a photosensitizer (e.g., a porphyrin or an active derivative thereof) and a targeting moiety that targets the conjugate to an infectious agent (e.g., a polypeptide, such as transferrin). The subject is irradiated with light, preferably using a wavelength that causes the photosensitizer to produce a cytotoxic effect. Preferably, the cytotoxic effect is substantial enough to kill at least 50%, more preferably at least 70%, and most preferably at least 90% of the pathogenic cells. The source of the irradiation can be any of the sources described herein, for example, a laser.

In another embodiment, the invention features a method of treating a subject having an infectious disease of the lung by administering to the subject a molecular conjugate that includes a photosensitizer (e.g., porphyrin or an active derivative thereof) and irradiating the lung with light having a wavelength that causes the photosensitizer to produce a cytotoxic effect. The molecular conjugate can also include a targeting moiety that targets the conjugate to an infectious agent (e.g., a polypeptide, such as transferrin). Those of skill in the art will recognize that the infectious disease of the lung can be associated with a bacterial infection (e.g., an infection associated with a *Mycobacterium* such as *M. tuberculosis*). In this or other methods described herein, the irradiation can be directed to the source of the infection. For example, in the event of a pulmonary infection, irradiation of the lung can be provided by a light source introduced into the passages through which air is inhaled. Alternatively, the irradiation of the lung can be provided by a light source introduced through the chest wall. Similarly, irradiation can be directed to particular regions of the body or particular parts of an organ or tissue. For example, in the event of a pulmonary infection, irradiation of the lung can be directed to the base of the lung, to the apex of the lung, or both.

The term "subject" is used herein to refer to a living animal, including a human, that carries an unwanted organism, the unwanted organism being the target of the therapeutic methods described herein. Accordingly, the unwanted organism may be referred to as the "target organism". The subject can be a mammal, such as a human or a non-human mammal (e.g., a dog, cat, pig, cow, sheep, goat, horse, rat, or mouse). The subject may be immune deficient; presently or previously undergoing treatment for cancer (e.g., by chemotherapy or radiation therapy); or presently or previously undergoing antibiotic therapy or an immunosuppressive therapy.

The intracellular pathogen may be contained within a host cell, such as a phagocyte (e.g., a macrophage). Further, within that cell, the pathogen may be contained (wholly or partly) within a vacuole, vesicle, or organelle.

Those of ordinary skill in the art will recognize disorders (or diseases or conditions) amenable to treatment with the present methods. The treatment may be effectively applied in the event a subject has a disease that is in a latent or an active stage. More specifically, disorders, diseases, or conditions amenable to treatment include, but are not limited to, tuberculosis and other disorders characterized by intrapulmonary granulomas, leprosy, MAI complex infections in AIDS patients, leishmaniasis and toxoplasmosis.

Once a molecular conjugate of the invention has been administered, the subject can be treated with irradiation. Typically, the irradiation (such as that generated by a laser) will have a wavelength that causes the photosensitizer (a part of the conjugate) to produce a cytotoxic effect (e.g., generation of toxic oxygen species, which can diffuse through the bacterial cell wall, or generation of reactive nitrogen intermediates). The photosensitizer can be a porphyrin or an active derivative thereof (i.e., a porphyrin that retains at least 50%, more preferably at least 80% (e.g., 85% or 90%), and most preferably at least 95% of the cytotoxic activity of the porphyrin from which it was derived). Assays by which this activity can be assessed are described further below. The photosensitizer can be chlorin e6.

To increase the specificity of the photosensitizer for its target, the photosensitizer may be bound to a targeting moiety. The targeting moiety can be a polypeptide (e.g., a human polypeptide such as poly-lysine or serum albumin). Alternatively, the targeting moiety can be a small antimicrobial peptide (i.e. a peptide containing less than 60 amino acid residues).

Also described further below are considerations relevant to administering the conjugate. These include routes of administration, including intravenous and parenteral (e.g., topical) administration. The conjugate can be administered to the lung in a variety of ways. For example it can be administered by way of the passages through which air is inhaled (i.e., it can be administered intratracheally, intrabronchially, or intraalveolarly). Alternatively, the conjugate can be administered through the body wall of the chest. The light that is applied to the conjugate once it has been administered can be applied through these routes as well (e.g., a light source, or a portion thereof, can be placed within the trachea, bronchi, or bronchioles of the lung or it can be inserted through the chest wall). The molecular conjugate may be administered to a subject on more than one occasion (i.e., at least twice). Similarly, a conjugate that has been administered can be illuminated on more than one occasion (i.e., at least twice), and the illumination (or irradiation) can be directed to the base of the lung, the apex of the lung, or both.

The invention also encompasses methods for making conjugate molecules, for example, by coupling a targeting moiety to a photosensitizer. The conjugate may further include a backbone to which both the targeting moiety and photosensitizer are coupled. The coupling reactions can involve an activated ester moiety of a photosensitizer. Alternatively, an amino group on the backbone may react as a nucleophile, displacing the leaving group from the photosensitizer active ester. Preferably, the targeting moiety is coupled to the backbone with a coupling agent.

In some embodiments, the conjugate does not include (i.e., it is not coupled, either covalently or non-covalently, to) an antibody, an enzyme, a hormone, a receptor on a cell surface, or the ligand for a receptor on a cell surface. However, in other embodiments, the conjugate can include (i.e., it can be coupled, either covalently or non-covalently, to) an antibody, an enzyme, a hormone, a receptor on a cell surface, or the ligand for a receptor on a cell surface.

Compositions of the invention are advantageous in that (i) they do not need to be internalized to bacteria to kill bacteria, (ii) the generation of toxic species (e.g., reactive oxygen intermediates or reactive nitrogen intermediates) can have a local effect in stimulating the host immune response, which in turn assists in eradicating bacteria and in promoting healing of the wound, and (iii) they produce a cytotoxic response only in the area subject to illumination.

BRIEF DESCRIPTION OF THE DRAWINGS

FIGS. 2A–2C are bar graphs representing the fraction of cells that survived following exposure to the molecular conjugates described along the X axis as cpd 33 5 µm, BPD non-liposomal 5 µm, BPD liposomal 5 µm, control, pl-ce6-ac-PEG 25 µm ce6 eq, pl-ce6-PEG 25 µm ce6 eq, pl-ce6-PEG 25 µm ce6 eq, pl-ce6- (dp 500) 25 µm ce6 eq, pl-ce6-(101ys, 1ce6) 25 µm ce6 eq (FIG. 2A), the uptake of each of the molecular conjugates (FIG. 2B, 10–10 mol PS/mg protein), and the resulting relative phototoxicity (FIG. 2C).

DETAILED DESCRIPTION

A. Molecular Conjugates

Figure 1:
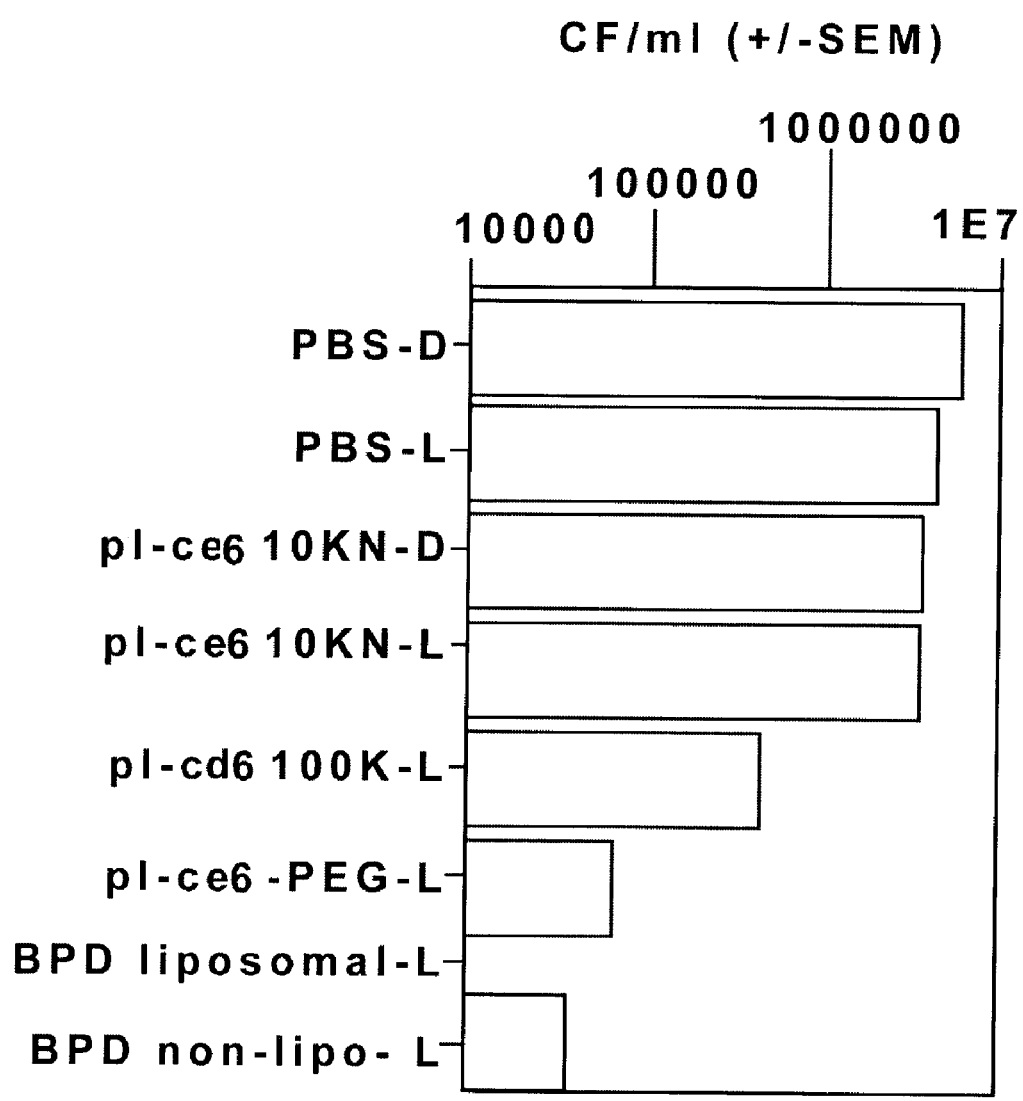
FIG. 1 is a bar graph representing the number of colony forming units (CFU/ml) formed by cells exposed to various molecular conjugates (specified along the Y axis) as BPD non-lipo-L, BPD liposomal-L, pl-ce6-PEG-L. pl-ce6 100K-L, pl-ce6 10KN-L, pl-ce6 10KN-D) and then to light (L) or dark (D).

The invention features molecular conjugates that include a photosensitizer coupled to a targeting moiety.

1. The Photosensitizer

A photosensitizer is a substance that produces a cytotoxic effect when irradiated with electromagnetic energy of an appropriate wavelength. Typically, a photosensitizer will be irradiated with light of an appropriate wavelength.

Many photosensitizers produce singlet oxygen. Upon electromagnetic irradiation at the proper energy level and wavelength, the photosensitizer is converted to an energized form that can react with atmospheric oxygen such that, upon decay of the photosensitizer to the unenergized state, singlet oxygen is produced. Singlet oxygen is highly reactive and is toxic to a proximal target organism, as are reactive nitrogen intermediates.

A molecular conjugate containing a photosensitizer should efficiently absorb electromagnetic energy of the appropriate wavelength with high quantum yield to efficiently generate the energized form of the photosensitizer. Toxicity to the target organism should increase substantially, preferably 10-fold, 100-fold, or even 1,000-fold upon irradiation. Ideally, a photosensitizer should exhibit low background toxicity, i.e., it should not be toxic in the absence of irradiation with energy of the appropriate wavelength. Further, a photosensitizer of the invention should be readily soluble in a variety of solvents, including those in which it is coupled to the targeting moiety and those in which it is administered to a subject. Those of ordinary skill in the art will recognize that what is desirable in the context of solubility will differ depending on the conditions in which the photosensitizer is coupled to form a conjugate (or the conditions in which the conjugate is administered). For example, the photosensitizer and targeting moiety may be coupled in a reaction requiring solubility in DMSO, water, ethanol, or a mixture thereof (e.g., a 1:1 mixture of DMSO:H$_2$O or 5% ethanol in water).

Photosensitizers include, but are not limited to, hematoporphyrins, such as hematoporphyrin HCl and hematoporphyrin esters (Dobson et al., *Arch. Oral Biol.* 37:883–887); dihematophorphyrin ester (Wilson et al., *Oral Microbiol. Immunol.* 8:182–187, 1993); hematoporphyrin IX and its derivatives (Russell et al., *Can. J. App. Spectros.* 36:103–107, available from Porphyrin Products, Logan, Utah); 3,1-meso tetrakis (o-propionamidophenyl) porphyrin; hydroporphyrins such as chlorin, herein, and bacteriochlorin of the tetra (hydroxyphenyl) porphyrin series, and synthetic diporphyrins and dichlorins; o-substituted tetraphenyl porphyrins (picket fence-porphyrins); chlorin e6 monoethylendiamine monamide (CMA; Goff et al. 70:474–480, 1994; available from Porphyrin Products, Logan, Utah); mono-1-aspartyl derivative of chlorin e6, and mono- and diaspartyl derivatives of chlorin e6; the hematoporphyrin mixture Photofrin II (quardra Logic Technologies, Inc., Vancouver, BC, Canada); benzophorphyrin derivatives (BPD), including benzoporphyrin monoacid Ring A (BPD-MA), tetracyanoethylene adducts, dimethyl acetylene dicarboxylate adducts, Diels-Adler adducts, and monoacid ring "a" derivatives; a naphthalocyanine (Biolo, *Photochem and Photobiol.* 5959:362–365, 1995); toluidine blue O (Wilson et al., *Lasers in Medical Sci.* 8:69–73, 1993); aluminum sulfonated and disulfonated phthalocyanine ibid.; and phthalocyanines without metal substituents, and with varying other substituents; a tetrasulfated derivative; sulfonated aluminum naphthalocyanines; methylene blud (ibid.); nile blue; crystal violet; azure β chloride; and rose bengal (Wilson, *Intl. Dent. J.* 44:187–189, 1994). Numerous photosensitizer entities are disclosed in Wilson et al., (*Curr. Micro.* 25:77–81, 1992) and in Okamoto et al. (*Lasers in Surg. Med.* 12:450–485, 1992).

Other potential photosensitizer compositions include but are not limited to, pheophorbides such as pyropheophorbide compounds, anthracenediones; anthrapyrazoles; aminoanthraquinone; phenoxazine dyes; phenothiazine derivatives; chalcogenapyrylium dyes including cationic selena- and tellura-pyrylium derivatives; verdins; purpurins including tin and zinc derivatives of octaethylpurpurin and etiopurpurin; benzonaphthoporphyrazines; cationic imminium salts; and tetracyclines.

The suitability of a photosensitizer for use in a conjugate can be determined by methods described herein or by methods known to those skilled in the art.

The efficiency with which a photosensitizer oxidizes a target molecule is a measure of its usefulness. The efficiency of the oxidation of a target molecule by a photosensitizer can be determined in vitro. Examples of substrates include 4-nitroso-N,N-dimethylaniline (RNO; Hasan, et al., *Proc. AACR* 28:395 Abstr. 1,568, 1987), and tryptophan or histidine (Lambert et al., *Photochem. Photobiol.* 44:595–601, 1986). In these assays, the ability of a candidate photosensitizer to "bleach" the substrate can be monitored spectroscopically. The advantage of a chemical assay is that a large number of putative photosensitizer compositions can be simultaneously screened. Parameters that can be varied include photosensitizer concentration, substrate concentration, optimal intensity of irradiation, and optimal wavelength of irradiation. High through-put technologies including plastic multi-well dishes, automated multi-pipetters, and on-line spectrophotometric plate readers can be used. Undesirable candidates, for example, compositions having high backgrounds under unirradiated conditions, inefficient energy capture or reactive potential, can be identified and eliminated.

In vivo assays with cells of one or more model target organisms can be used to evaluate a photosensitizer for cytotoxicity of its background and activated forms. The efficiency of killing of the organism in the presence of the irradiated and unirradiated photosensitizer can be measured and compared to survival of the untreated control cell sample. This assay can be automated. The use of counts of colony forming units (CFU) or cell growth may require incubation of the samples that have been applied to a nutrient medium, with a concomitant lag of the appropriate growth period to allow for colony formation.

Survival of cells of the model target organism can alternatively be monitored by assay of a biochemical process, for example, assay of DNA synthesis. In this approach, the effectiveness of a photosensitizer candidate can be measured by its effect on samples of cells of the model organism, which are also exposed to a labeled DNA precursor such as tritiated thymidine. Cells are then collected, washed to remove unincorporated precursor, and monitored for uptake of the precursor and incorporation into acid-insoluble precipitate, which is a measure of quantity of DNA synthesis. In this assay, which can also be automated, quantitative evaluation of the effects of presence of irradiated photosensitizer compositions can be readily evaluated and quantitated. In control unirradiated cells and in untreated cells, DNA synthesis increases logarithmically as a function of cell growth. A positive result indicating presence of a putative successful novel photosensitizer, is turn-off of DNA synthesis in cells that have been irradiated in the presence of that photosensitizer.

Alternatively, survival of the target organism can be monitored by measuring the incorporation of [$^3$H] uracil into nucleic acids of the organism. This measurement can be made as described, for example, by McLeod and Remington (*J. Immunol. Meth.* 27:19–29, 1979). This assay can be used when the target organism is of the genus Toxoplasma, e.g., *T. gondii*.

If large numbers of candidates are to be screened it may be desirable to use a two-stage screen, wherein the first stage is an in vitro screen and the second stage employs cells.

A suitable positive control for photosensitizer activity is toluidine blue O.

2. The Targeting Moiety

The targeting moiety can be a molecule or a macromolecular structure that targets macrophages or that interacts with a pathogen. Thus, in some embodiments, the photosensitizer is also the targeting moiety. For example, some photosensitizers target macrophages directly (see, e.g., Korbelik et al., *Cancer Res.* 51:2251–2255, 1991). Moieties, a target moiety alone or incorporated into a conjugate, can be a supramolecular structure (e.g., a liposome, a micelle, a lipid vesicle, or the like) can be used to specifically target macrophages by certain receptors. Thus, a ligand for such receptors can be used as a targeting moiety. For example, the following receptors can be used to target macrophages: the complement receptor (Rieu et al., *J. Cell Biol.* 127:2081–2091, 1994), the scavenger receptor (Brasseur et al., *Photochem. Photobiol.* 69:345–352, 1999; Suzuki et al., *Nature* 386:292–296, 1997; Sarkar et al., *Mol. Cell. Biochem.* 156:109–116, 1996), the transferrin receptor (Dreier et al., *Bioconjug. Chem.* 9:482–489, 1998; Hamblin et al., *J.*

Photochem. Photobiol. 26:45–56, 1994; Clemens et al., J. Exp. Med. 184:1349–1355, 1996), the Fc receptor (Rojanasakul et al., Pharm. Res. 11:1731–1733, 1994; Harrison et al., Pharm Res. 11:1110–4, 1994). The mannose receptor is particularly important for macrophage recognition of foreign material and has been used successfully to target molecules to macrophages (Frankel et al., Carbohydr. Res. 300:251–258, 1997; Chakrabarty et al., J. Protozool. 37:358–364, 1990; Mistry et al., Lancet 348:1555–1559, 1996; Liang et al., Biochim. Biopys. Acta 1279:227–234, 1996; Sarkar et al., Mol. Cell Biochem. 156:109–116, 1996). Toll or toll-like receptors are also present on macrophages and are useful targets (Brightbill et al., Science 285:732–736, 1999).

Moieties that can be conjugated with photosensitizers in order to target to macrophages include low density lipoproteins (Mankertz et al., Biochem. Biophys. Res. Commun. 240:112–115, 1997; von Baeyer et al., Int. J. Clin. Pharmacol. Ther. Toxicol. 31:382–386, 1993), very low density lipoproteins (Tabas et al., J. Cell Biol. 115:1547–1560, 1991), mannose residues (as mentioned above) and other carbohydrate moieties (Pittet et al., Nucl. Med. Biol. 22:355–365, 1995), poly-cationic molecules (e.g., poly-L-lysine; Hamblin et al., J. Photochem. Photobiol. 26:45–56, 1994), emulsions (Khopade et al., Pharmazie 51:558–562, 1996), aggregated albumin (Hamblin et al., J. Photochem. Photobiol. 26:45–56, 1994), biodegradable microspheres (Oettinger et al., J. Interferon Cytokine Res. 19:33–40, 1999), non-biodegradable microspheres (Schroder, Methods Enzymol 112:116–128, 1985), nanoparticles (Lobenberg et al., AIDS Res. Hum. Retroviruses 12:1709–1715, 1996); Venier-Julienne et al., J. Drug Target. 3:23–29, 1995; Schafer et al., J. Microencapsul. 11:261–269, 1994; Gaspar et al., Ann. Trop. Med. Parasitol 86:41–49, 1992), liposomes (Bakker-Woudenberg et al. J. Drug Target. 2:363–371, 1994; Meyers et al., Exp. Lung Res. 19:1–19, 1993; Betageri et al., J. Pharm. Pharmacol. 45:48–53, 1993; Muller et al., Biochim. Biophys. Acta. 986:97–105, 1989; Kole et al., J. Infect. Dis. 180:811–820, 1999), macrophage-specific cytokines (Biragyn et al., Nat. Biotechnol. 17:253–258, 1999; Chan et al., Blood 86:2732–2740, 1995), erythrocytes (Magnani et al., J. Leukoc. Biol. 185:717–730, 1997), antibodies recognizing critical components of the tuberculous phagosome like Nrampl (Gruenheid et al., J. Exp. Med. 185:717–730, 1997), α 2-macroglobulin (Chu et al., J. Immunol. 152:1538–1545, 1994).

A targeting moiety can be directed to the infectious pathogen (e.g., mycobacteria). For example, conjugates that couple relevant anti-mycobacterial antibiotics, such as isoniazid, to the photosensitizers can be used (Quenard et al., Biochemistry 34:8235–8241, 1995). In addition, certain structural features of critical enzymes can be targeted, such as the hydrophobic pocket of the Mycobacterium tuberculosis enzyme inhA (Dessen et al., Science 267:1638–1641, 1995). Alternatively, host molecules that target the bacteria, such as anti-microbial peptides (e.g., granulysin), can be used in conjugates (Stenger et al., Science 282:121–125, 1998).

A targeting moiety can be used alone or in combination, particularly to target both macrophages and the intracellular pathogen (e.g., mycobacteria). Manipulations of the host cell can also complement the photosensitizer (Collins et al., J. Cell Sci. 110:191–200, 1997; Korbelik et al., Br. J. Cancer 75:202–207, 1997; Krosl et al., Cancer Res. 56:3281–3286, 1996).

The targeting moiety can be a polypeptide (which may be linear, branched, or cyclic). The targeting moiety can include a polypeptide having an affinity for a polysaccharide target, for example, a lectin (such as a seed, bean, root, bark, seaweed, fungal, bacterial, or invertebrate lectin). Particularly useful lectins include concanavalin A, which is obtained from jack beans, and lectins obtained from the lentil, Lens culinaris.

B. The Target Organism

An organism that is targeted for destruction by the methods and compositions described herein is an unwanted organism; unwanted in that it infects a host organism (or a cell thereof) and causes or aggravates a disease or disorder in that host. Especially preferred target organisms are bacterial cells, particularly of the genera Mycobacteria and Toxoplasma, and viruses.

Organisms to be targeted by the compositions and methods of the present invention can be found on any light-accessible surfaces or in light-accessible areas, for example, in human and animal subjects, materials to be decontaminated, or on crop plants. In the cases of humans and animals, infections of the epidermis, oral cavity, nasal cavity, sinuses, ears, lungs, urogenital tract, and gastrointestinal tract are light accessible. Epidermal infections include those of unwanted organisms of bacterial, fungal, viral and animal origin, and include subcutaneous infections, especially localized lesions, for example caused by protozoans, parasites, or parasitic mites, which infections are light-accessible. Infections of the peritoneal cavity, such as those resulting from burst appendicitis, are light accessible via at least laparoscopic devices. A variety of skin infections which are refractory to antibiotics or long-term antifungal treatment, for example, dermatophycoses of the toenail, are suitable for photodynamic therapy using the methods and compositions of the invention.

Lung infection can occur with a variety of bacterial genera and species, which include the classical tuberculosis of Mycobacterium tuberculosis, the pseudomonads, which are the primary cause of death of cystic fibrosis patients, Klebsiella, and can also occur with a variety of virus strains. A variety of fungi and parasites are opportunistic pathogens of the lung, and Pneumocystis carinii infection is a common cause of death in immunocompromised AIDS patients. As pathogens of the lung are increasingly resistant to classical antibiotic therapies, photodynamic therapy with the compositions of the instant invention offer an alternative method for eliminating these unwanted organisms that is independent of the microbial mechanisms of resistance.

C. Administering the Molecular Conjugates of the Invention to a Host Organism

When a photosensitizer is linked to a targeting moiety, the resulting conjugate should be soluble under physiological conditions, in aqueous solvents containing appropriate carriers or excipients, or in other systems, such as liposomes, that may be used to administer the conjugate to a subject.

The molecular conjugates of the invention can be delivered to a subject in a free form, i.e., as a conjugate in solution. Alternatively the conjugates can be delivered in various formulations including, but not limited to, liposome, peptide-bound, polymer-bound, or detergent-containing formulations. Those of ordinary skill in the art are well able to generate and administer such formulations (see also, below).

The conjugates of the invention should be stable during the course of at least a single round of treatment by continuous or pulsed irradiation, during which the photosensitizer within the conjugate would, preferably, be repeatedly excited to the energized state, undergoing multiple rounds of generation of singlet oxygen.

The compounds of the invention include conjugate molecules that have been formulated for topical administration, and also for administration to various external organs such as the outer ear, or organs accessible by external administration, such as by oral application or by lavage of the lung. The examples mentioned here are not intended as limiting with respect to the nature of the conjugate photosensitizer compositions of the invention, or to a particular route of the administration, and additional routes are listed herein. In another embodiment of the present invention, the photosensitizer compositions can be administered by combination therapy, i.e., combined with other agents. For example, the combination therapy can include a composition of the present invention with at least one other photosensitizer, at least one antibiotic, or other conventional therapy.

Photosensitizer conjugates that are somewhat insoluble in an aqueous solvent can be applied in a liposome, or a time release fashion, such that illumination can be applied intermittently using a regimen of periods of illumination alternating with periods of non-illumination. Other regimens contemplated are continuous periods of lower level illumination, for which a time-release formulation is suitable.

As used herein, the phrase "pharmaceutically acceptable carrier" includes any and all solvents, dispersion media, coatings, antibacterial and antifungal agents, isotonic and all solvents, dispersion media, coatings, antibacterial and antifungal agents, isotonic and absorption delaying agents, and the like that are physiologically compatible. The use of such media and agents for pharmaceutically active substances is well known in the art. Preferably, the carrier is suitable for oral, intravenous, intramuscular, subcutaneous, parenteral, spinal or epidermal administration (e.g., by injection or infusion). Depending on the route of administration, the active compound may be coated in a material to protect the compound from the action of acids and other natural conditions that may inactivate the compound.

Conjugates of the invention can also be administered parenterally. The phrase "administered parenterally" as used herein means modes of administration other than oral administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

A composition of the present invention can be administered by a variety of methods known in the art. As will be appreciated by the skilled artisan, the route and mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Dosage regimens are adjusted to provide the optimum desired response (e.g., a therapeutic response). For example, a single bolus may be administered, several divided doses may be administered over time, or the dose may be proportionally reduced or increased as indicated by the exigencies of the therapeutic situation.

One of ordinary skill in the art can determine and prescribe the effective amount of the pharmaceutical composition required. For example, one could start doses of the known or novel photosensitizer composition levels lower than that required in order to achieve the desired therapeutic effect and gradually increase the dosage until the desired effect is achieved.

Irradiation of the appropriate wavelength for a given compound may be administered by a variety of wavelengths. Methods for irradiation include, but are not limited to, the administration of laser, nonlaser, or broad band light. Irradiation can be produced by extracorporeal or intraarticular generation of light of the appropriate wavelength. Light used in the invention may be administered using any device capable of delivering the requisite power of light including, but not limited to, fiber optic instruments, arthroscopic instruments, or instruments that provide transillumination. Delivery of the light to a recessed, or otherwise inaccessible physiological location can be facilitated by flexible fiber optics (implicit in this statement is the idea that one can irradiate either a broad field, such as the lung or a lobe of the lung, or a narrow field where bacterial cells may have localized). The source of the light needed to inactivate the bacteria can be an inexpensive diode laser or a non-coherent light source.

EXAMPLES

The studies that follow were performed with *Mycobacterium bovis* BCG that was grown in liquid culture (7H9 medium), incubated with a photodynamic compound, aliquoted into the wells of a 96-well tissue culture plate and exposed to light (for one hour at 80 J/cm). (Control experiments are described below). To assess the effect of this treatment on cytotoxicity, the bacteria, in suspension, were diluted by ten-fold-dilutions, and 10 $\mu$l aliquots were spotted onto agar plates (7H10 medium). The number of colony forming units (CFUs) were counted 7–10 days later.

More specifically, for each photodynamic compound tested, 100 $\mu$l of a liquid *M. bovis* culture ($OD_{600}$=1) was transferred to an Eppendorf tube, which was centrifuged to pellet the bacterial cells. The medium was then discarded and the cells were resuspended in either 1 ml of medium or 1 ml of 7H9 broth. The resulting concentration of cells was approximately $1\times10^6$ cells/ml. Once resuspended, the photodynamic compound (or, as a control, an equivalent volume of PBS) was added to the cell suspension. The following photodynamic compounds were tested in this study: pl-ce6, BPD, and cpd 33.

The cells were incubated with the photodynamic compounds and then aliquoted (in 200 $\mu$l aliquots) onto a microtiter plate, in duplicate. The first set of samples was exposed to light (for one hour at 80 J/cm), but the duplicate set remained in the dark. Each sample was then serially diluted and 10 $\mu$l of each dilution was spotted, in triplicate, onto a mycobacterial agar plate. The plates were allowed to dry and then incubated for 7–10 days at 37° C. At the conclusion of the incubation period, colony forming units were counted.

The results obtained are shown in FIG. 1. The number of CFUs was clearly reduced in all samples that were incubated with a photodynamic compound and exposed to light (L; D=dark) except for the sample incubated with cpd33 (which was toxic to BCG regardless of whether or not the cells were exposed to light (data not shown). While only modest cytotoxicity was evident in the samples treated with pl-ce6-

PEG and BPD "non-liposomal," these compounds reduced the size of the colonies that were formed and altered their morphology.

The study described above was repeated and the results were analyzed in terms of the number of cells killed relative to the apparent uptake of the photodynamic compound. These data are shown in FIGS. 2A and 2B and the relative phototoxicity of the compounds is shown in FIG. 2C.

Other Embodiments

Other embodiments are described in the text that is appended to, and part of, the specification. The present invention is not to be limited in scope by the specific embodiments described, which are intended as single illustrations of individual aspects of the invention. Functionally equivalent methods and compositions are within the scope of the invention, and will become apparent to those skilled in the art from the foregoing description. Such functional equivalents are intended to fall within the scope of the appended claims.

What is claimed is:

1. A method of killing an intracellular pathogen, the method comprising contacting a cell containing an intracellular pathogen selected from the group consisting of a *Toxoplasma*, a *Listeria*, a *Salmonella* and a *Leischmania* with a photosensitizer and irradiating the cell, the irradiation having a wavelength that causes the photosensitizer to produce a cytotoxic effect, thereby killing the intracellular pathogen.

2. The method of claim 1, wherein the photosensitizer is pl-ce6 or BPD.

3. The method of claim 1, wherein the photosensitizer is selected from the group consisting of a chlorin, purpurin, porphyrin or an active derivative thereof, pthalocyanine and phenothiazine.

4. The method of claim 3, wherein the chlorin is chlorin e6.

5. The method of claim 3, wherein the porphyrin is a benzophorphyrin derivative.

6. The method of claim 3, wherein the purpurin is tinetiopurpurin.

7. The method of claim 3, wherein the chlorin is meta-tetrahydroxyphenyl chlorin.

8. The method of claim 3, wherein the porphyrin is an ALA-induced protoporphyrin.

9. The method of claim 3, wherein the photosensitizer is a cationic photosensitizer.

10. The method of claim 9, wherein the cationic photosensitizer is selected from the group consisting of a chlorin, porphyrin or an active derivative thereof, pthalocyanine and phenothiazine.

11. The method of claim 1, wherein the intracellular pathogen is a *Toxoplasma*.

12. The method of claim 1, wherein the intracellular pathogen is a *Listeria*.

13. The method of claim 1, wherein the intracellular pathogen is a *Salmonella*.

14. The method of claim 1, wherein the intracellular pathogen is a *Leischmania*.

* * * * *